United States Patent [19]

Makino

[11] Patent Number: 4,589,121
[45] Date of Patent: May 13, 1986

[54] DENTAL PANORAMIC X-RAY PHOTOGRAPHING APPARATUS

[75] Inventor: Takao Makino, Otsu, Japan

[73] Assignee: Kabushiki Kaisha Morita Seisakusho, Kyoto, Japan

[21] Appl. No.: 695,099

[22] Filed: Jan. 25, 1985

[30] Foreign Application Priority Data

Feb. 1, 1984 [JP] Japan ................... 59-17895

[51] Int. Cl.$^4$ ....................... G03B 41/16; H05G 1/32
[52] U.S. Cl. ........................................ 378/39; 378/40
[58] Field of Search ............................. 378/38, 39, 40

[56] References Cited

U.S. PATENT DOCUMENTS

| 4,063,099 | 12/1977 | Grassmé378 | 39/ |
| 4,333,012 | 6/1982 | Furuichi | 378/38 |
| 4,430,746 | 2/1984 | Suzuki et al. | 378/40 |

*Primary Examiner*—Alfred E. Smith
*Assistant Examiner*—T. N. Grigsby

*Attorney, Agent, or Firm*—Koda and Androlia

[57] ABSTRACT

A dental panoramic X-ray photographing apparatus including a rotary arm having an X-ray generator disposed at one end thereof and having an X-ray film cassette holder disposed at the other end thereof in an opposite relation with each other around an object disposed therebetween. The apparatus comprises a first control means for controlling the rotation speed of the arm by detecting the rotation position of the arm and a second control means for controlling the tube voltage and the tube current of the X-ray generator by comparing the feeding speed of the X-ray film at the X-ray film cassette holder with the residual X-ray dose which has passed the object and the film, whereby it is intended to provide the simultaneous control function of the tube voltage and the tube current, the function for automatic exposure throughout the entire teeth and the function for compensating for the density of the central portion of the front tooth region of a dental arch at the same time.

2 Claims, 7 Drawing Figures

DENTAL PANORAMIC X-RAY PHOTOGRAPHING APPARATUS

BACKGROUND OF THE INVENTION

1. Field of the Invention

This invention relates to improvements in a dental panoramic X-ray photographing apparatus, and more particularly to a dental X-ray photographing apparatus for entire jaws for dental diagnosis including a rotary arm having an X-ray generator disposed at one end thereof and having an X-ray film cassette holder disposed at the other end thereof in an opposed relation with each other, with an object disposed therebetween, whereby panoramic X-ray photographing can be performed as the rotary arm rotates.

2. Prior Art

A dental panoramic X-ray photographing apparatus disclosed by the Japanese Provisional Patent Publication No. 58-83939 has a function generator which determines the speed of a photographing unit to comparatively reduce the control range of X-ray tube voltage when the X-ray tube voltage is used as a dose output control value, whereby the speed pattern which ensures application of a constant X-ray dose to an X-ray film is memorized by the function generator. Although this conventional apparatus has been effective in its own way, it has the following problems to be solved.

(1) The rotation speed of the rotary arm of the apparatus is determined by the signal from the function generator. If the rotation position of the rotary arm is dislocated, however, the rotation speed of the rotary arm is changed at the dislocated position different from the regular position. If the rotation speed is decreased at the position slightly dislocated from the regular position suited to photograph the front tooth region and the X-ray dose is increased for example, the density of the image obtained on the film increases at positions different from the front tooth region and decreases at other positions. Moreover, if the rotary arm is rotated halfway and returned to its start position for some reason, the rotation speed of the rotary arm must also respond to the rotation position of the rotary arm.

(2) Since the feeding speed of the X-ray film is not compared with the X-ray transmission dose, photographing may not be performed satisfactorily due to slipage of mechanical part and the motor's follow-up errors.

(3) Since the tube current of the apparatus is not automatically controlled, the apparatus cannot follow up any great change in a tooth shape due to a lack of a bone for example.

SUMMARY OF THE INVENTION

It is therefore an object of the present invention to provide a dental panoramic X-ray photographing apparatus which can solve the above problems.

Generally speaking, the apparatus has a function to simultaneously control the tube voltage and the tube current, an automatic exposure function for all teeth and a function to compensate for the density at the central portion of the front tooth region of a dental arch.

An embodiment of the present invention will be apparent from the following description and the accompanying drawings.

DETAILED DESCRIPTION OF THE INVENTION

Figure 1:
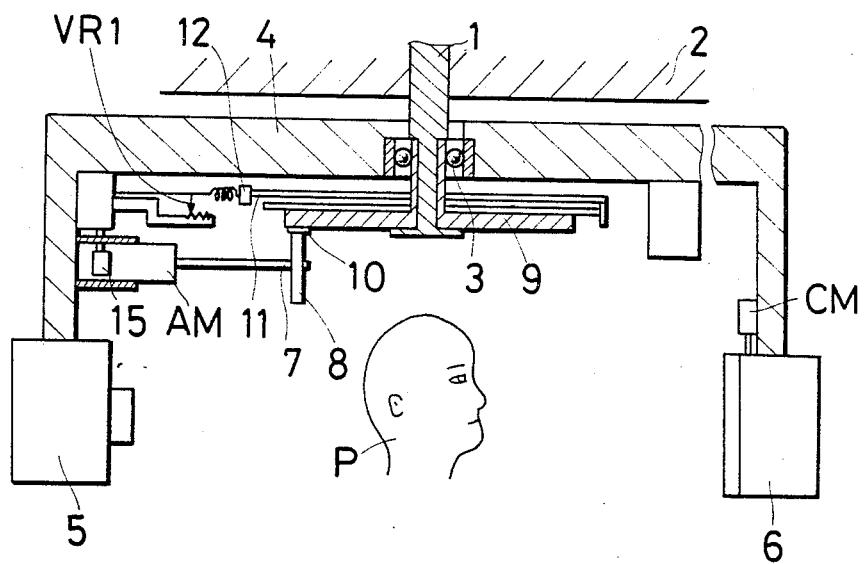
FIG. 1 is a longitudinal sectional side view of one embodiment of the present invention.
Figure 2:
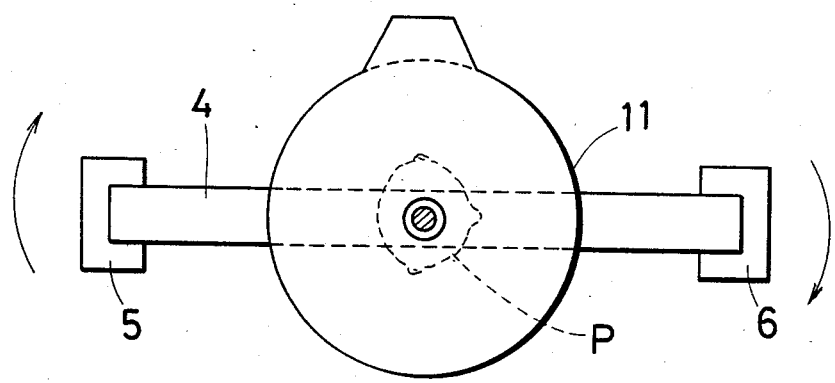
FIG. 2 is a plan view of FIG. 1.

Referring now to the structure of the dental panoramic X-ray photographing apparatus, the numeral 1 in FIGS. 1 and 2 designates a base shaft 1 suspended from a support base 2 and a rotary arm 4 is suspended through a bearing 3 on the base shaft 1 so as to permit the free horizontal rotation thereof. An X-ray generator 5 is held at one end of the arm 4 and an X-ray film cassette holder 6 is held at the other end thereof at an angle phase of 180 degrees in an opposed relation with respect to the generator. At the time of photographing, the arm rotatingly travels within the same plane area in which the generator 5 and the cassette holder 6 having an object P disposed therebetween surrounds the object P in such a manner that the feeding of an X-ray film is effected in the film holder 6 in synchronism with the rotation speed of the rotary arm. The rotary arm is integrally provided with an arm motor AM (referred to hereinafter as a motor AM) for rotatingly moving the rotary arm 4 and also provided on the drive shaft 7 of the motor AM with a pinion 8, while the lower section of the base shaft 1 is fixedly mounted with a receiving plate 9. On the under side of the plate 9 is fixed a rack 10 circumferentially around the base shaft 1. The pinion 8 and the rack 1 are mated with each other, and the rotary arm 4 is forced to rotate in accordance with the rotation of the pinion 8 on the rack 10 by rotation of the motor AM.

Furthermore, the rotary arm 4 is mounted with a film feeding motor CM for feeding the X-ray film. The numeral 11 designates a cam plate placed detachably on the top of the receiving plate 9. The cam plate 11 depresses a plunger 12 by rotation of the rotary arm 4, which depression, in turn, changes the resistance value of the variable resistor VR1 (FIG. 1) of an arm position detection circuit 34 in FIGS. 3, 4 and 5. By this change, the rotation position of the rotary arm 4 is obtained as an electrical rotation position signal. This rotation position signal is input to a rotary arm rotation speed setting circuit 13 shown in FIG. 3, and the rotation speed command corresponding to the rotation position is input to an arm motor control circuit 14 to control the motor AM at the proper rotation speed. This is how the first control means A1 of the apparatus of the present invention functions.

Figure 3:
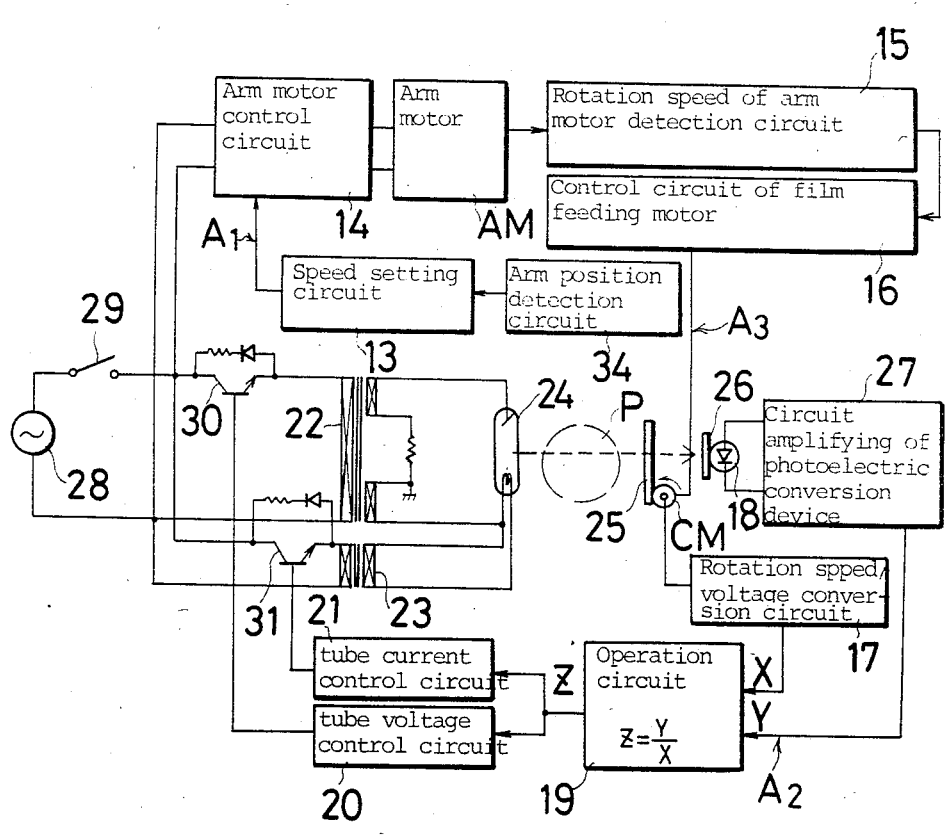
FIG. 3 is a circuit diagram of the embodiment of the present invention.
Figure 4:
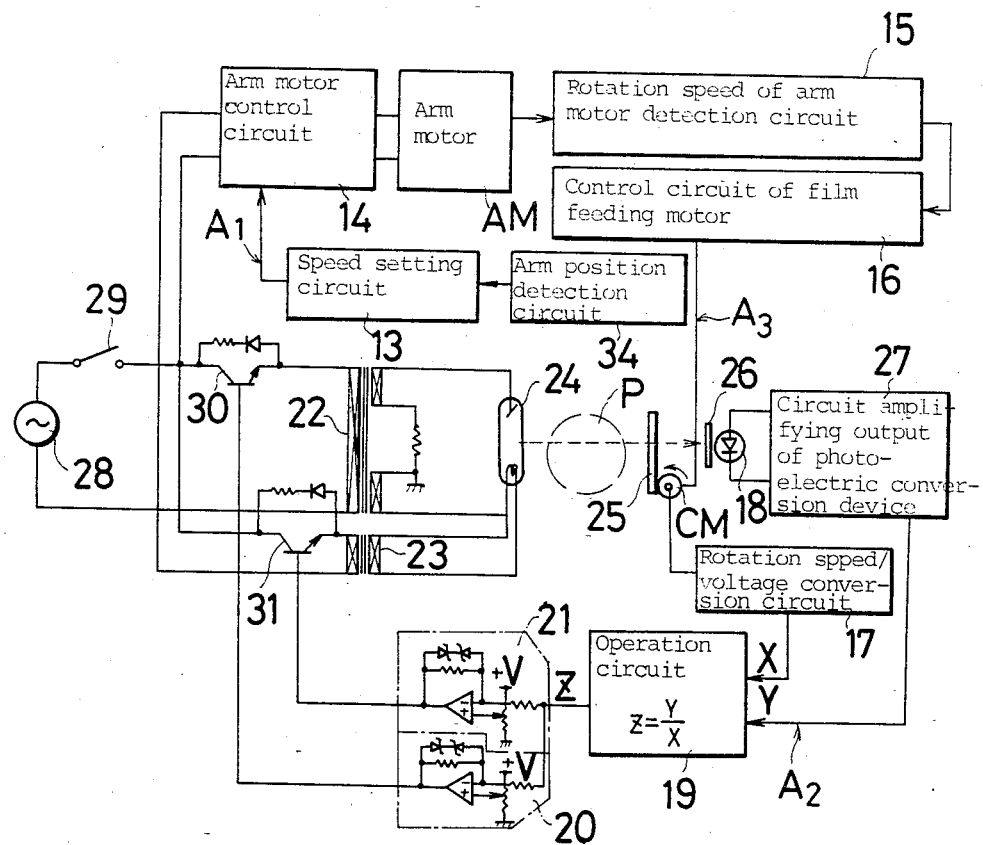
FIG. 4 is a first concrete circuit digram of FIG. 3.
Figure 5:
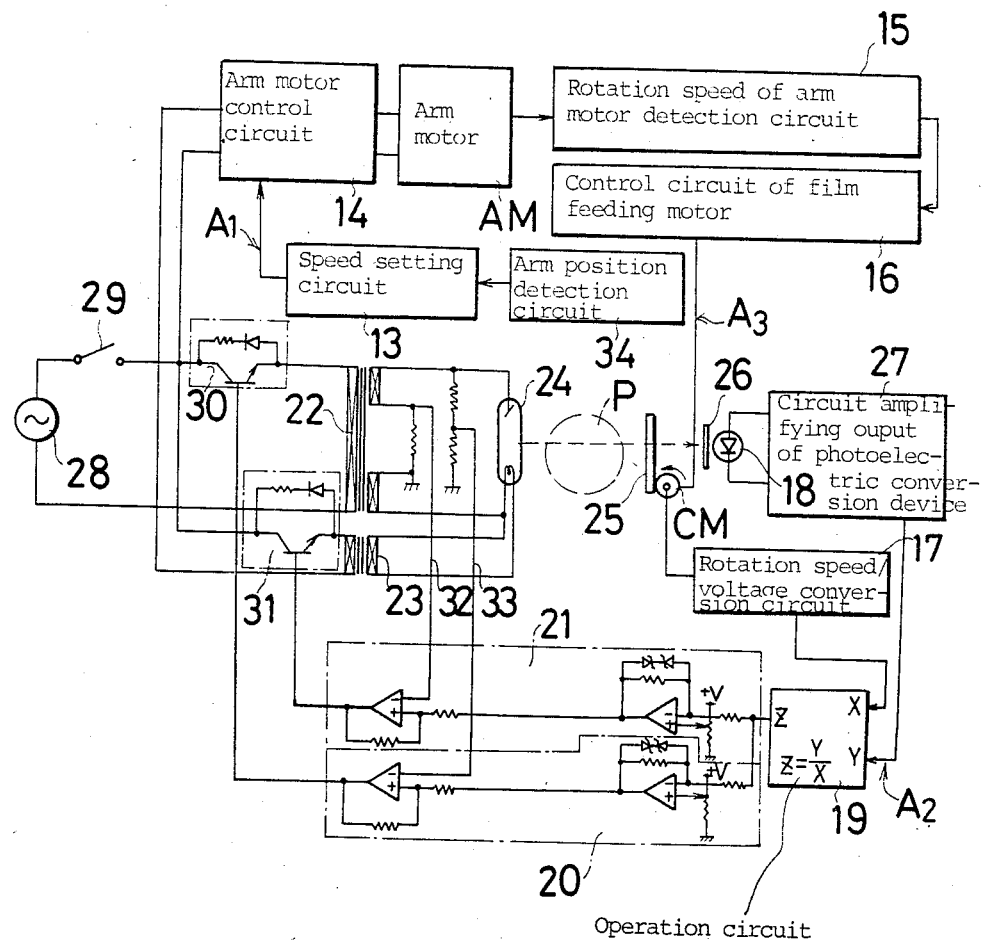
FIG. 5 is a second concrete circuit diagram of FIG. 3.

Referring to FIG. 1 again, the motor AM is connected to a rotation speed detection circuit which includes a tachogenerator or a combination of a pulse generator and a counter. The rotation speed signal of the motor AM is always generated and input to the control circuit 16 of the film feeding motor CM. Thus, the feeding speed of the film feeding motor CM is synchronously changed in proportion to the rotation speed of the motor AM, which is also in proportion to the rotation speed of the rotary arm, that is, the rotation speed of the X-ray generator 5 so that the feeding speed of the X-ray film can be properly controlled. This is how the third control means A3 of the apparatus of the present invention functions. In the second control means A2 of the apparatus of the present invention an X-ray film feeding speed is taken out by a rotation speed/voltage conversion circuit 17, such as a low-speed tachometer shown in FIG. 3, and the residual X-ray dose which has passed the object P and the X-ray film 25 is taken out by a photoelectric conversion device 18 shown in FIGS. 3, 4 and 5. The ratio of the output signals from both are operated by an operation circuit 19 so that the X-ray tube voltage kV and the X-ray tube current mA are simultaneously fed back through control circuits 20 and 21 respectively. The X-ray generator 5 composed of high-voltage devices, i.e., a high-voltage transformer 22, a filament transformer 23 and an X-ray tube 24 shown in FIGS. 3, 4 and 5 is included in an X-ray irradiation head. The X-ray film cassette holder 6 including an X-ray film 25 is provided at an angle phase of 180 degrees in an opposed relation with respect to the head. The X-ray film cassette holder 6 also includes a low-speed tachometer 17 which detects the feeding speed of the film 25 and outputs an electrical signal corresponding to the speed, a fluorescent plate 26 which emits light when it is excited by the X-ray which has passed the object P and the film 25, and a photoelectric conversion device 18 which outputs an electrical signal depending on the light emission brightness of the fluorescent plate 26. The numeral 27 designates a circuit which amplifies the output of the photoelectric conversion device 18. The output of the rotation speed/voltage conversion circuit 17 and the output of the photoelectric conversion device 18 through the amplifier circuit 27 are input to the operation circuit 19. This operation circuit 19 outputs a ratio signal (z=y/x) of both output signals. On the head side, both the primary of the high-voltage transformer 22 and the primary of the filament transformer 23 are connected to an AC power source 28 through an on/off switch 29. A feedback control transistor 30 is provided at the primary of the high voltage transformer 22 and a feedback control transistor 31 provided at the primary of the filament transformer 23. The high-voltage transformer 22 and the filament transformer 23 are feedback-controlled by changing the base biases (conduction angles) of the feedback control transistors 30 and 31. For this purpose, the output of the operation circuit 19 is fed to both the tube voltage control circuit 20 and the tube current control circuit 21 and the aforesaid base biases are adjusted by these circuits 20 and 21.

When the apparatus of the present invention is used, the arm rotation speed setting circuit 13 in the first control system A1 is set so that the rotation speed of the rotary arm 4 at the front tooth region is slower than that at other regions. This setting is necessary to compensate for the maximum rating of the X-ray dose irradiated to the front tooth region, which might not be enough to obtain satisfactory X-ray images, since the X-ray is irradiated through the cervical vertebrae of the object patient when the front tooth region is photographed. In other words, the rotation speed of the rotary arm 4 is decreased at the front tooth region to compensate for the insufficient intensity of the X-ray by increasing the X-ray irradiation dose. This is the socalled front tooth region density compensation. In the second control system A2, the ratio between the tube voltage and the tube current is properly determined. That is, the circuits in FIG. 3 are designed to adjust the control circuits 20 and 21 so that a specified relationship is obtained between the tube voltage and the tube current; a tube current of 5 mA flows when a tube voltage of 60 kV is applied and a tube current of 10 mA flows when a tube voltage of 80 kV is applied, for example. The ratio should be determined according to clinical data.

As photographing begins, the output of the variable resistor VR1 is changed by the cam plate 11 which rotates together with the rotary arm 4 and a rotary arm position signal is delivered. Thus, the motor AM is controlled so that the rotary arm 4 is rotated at the rotation speed corresponding to the position signal. The rotation speed of the motor AM is fed to the third control system A3 and the rotation speed of the film feeding motor CM is changed depending on the rotation speed of the motor AM. Therefore, the X-ray film 25 can be fed at the speed corresponding to the rotation speed of the rotary arm 4. The X-ray passes through the teeth of the object P and exposes the film 25 to form images on the film 25. As the fluorescent plate 26 is excited by the residual X-ray dose which has passed through the film and emits light, an electrical signal corresponding to the brightness of the light (X-ray intensity) is input to the operation circuit 19 of the control system A2. At the same time, the feeding speed signal of the X-ray film which is fed by the film feeding motor CM is input to the operation circuit 19. The operation circuit 19 feeds the signal of the ratio of the two input signals (Z=y/x) to the control circuits 20 and 21. The control circuits 20 and 21 compare the ratio value from the operation circuit 19 with their predetermined ratio value. The high voltage transformer 22 and the filament transformer 23 are driven by changing the base biases of the feedback control transistors 30 and 31 so that the ratio value from the operation circuit 19 cooincides with the predetermined ratio value. More specifically, by changing the voltage and filament current applied to the X-ray tube 24, the tube voltage and the tube current are simultaneously fed back to make the output signal (z=y/x) of the operation circuit 19 constant. By this feedback control, a fixed relationship is maintained between the tube voltage and the tube current (60 kV and 5 mA for example) as a matter of course, even though both change. By maintaining the value z constant, an image can have the best quality and contrast. When the front tooth region is irradiated by the X-ray, the rotation speed of the motor Am is decreased by the position detection operation of the rotary arm 4 and the rotation speed of the rotary arm 4 drops. As a result, the X-ray irradiation dose at the front tooth region increases to compensate for the X-ray dose which is lost when the X-ray passes through the cervical vertebrae. Accordingly, the X-ray irradiation dose at the front tooth region is approximately identical to that at the molar tooth region and thus an image uniform in density can be obtained. FIGS. 4 and 5 are concrete circuits of FIG. 3. In FIG. 4, a comparator is used to compare the output of the operation circuit 19 with the set value which has been determined so that the best suited tube voltage and tube current are obtained. The tube voltage and the tube current are respectively fed back by the tube voltage feedback control transistor 30 and the tube current feedback control transistor 31 located at the primaries of the high voltage transformer 22 and the filament transformer 23. In the example shown in FIG. 5, the tube voltage and the tube current actually applied to the X-ray tube 24 are taken out and input to the control circuit 20 and 21.

By comparing the feedback value fed from the operation circuit 19 with the reference value, the feedback control value is compensated for so that the X-ray photographing is not affected by the change of the power supply voltage even when the actual tube voltage and the tube current are changed due to the change of the power supply voltage.

Figure 6:
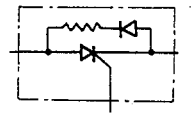
FIGS. 6 and 7 are other examples of feedback voltage control devices.
Figure 7:
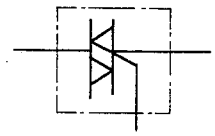

Instead of using transistors 30 and 31 as a tube voltage feedback control device and a tube current feedback control device in FIGS. 3, 4 and 5, any devices which can control the voltages of the feedback circuits can be used. Therefore, a thyristor shown in FIG. 6 and a triac shown in FIG. 7 can also be used.

The tube voltage control circuit 20 and the tube current control circuit 21 are not detailed in this specification, since they were applied as the Japanese Patent Application No. 58-142045 filed on Aug. 2, 1983 and the Japanese Utility Model Application No. 58-190748 filed on Dec. 10, 1983 and are now pending. These applications have not yet been provisionally published as of now.

The cam plate 11 and the variable resistor VR1 used to detect the rotation position of the rotary arm in the above description can be replaced with a disc, a pulse generator and a counter (not shown) so that the pulse generator may generate pulses by reading preformed surface configurations (convex and concave) and marks on the disc. Accordingly, the present invention can be applied to both analog and digital signal systems. Furthermore, instead of the rotary arm motor AM integrated with the rotary arm in the aforesaid embodiment, a separated motor from arm can also be used as described in the Japanese Provisional Patent Publication No. 56-83335. With this invention, the image density of the X-ray film can be made uniform by simultaneous feedback control of the tube voltage and the tube current as described above to obtain a high-quality image and to allow a dentist to make exact diagnosis. In addition, since it is not necessary to press either of the tube voltage or the current to any fixed value like the prior art, no setting error occurs and a high-quality image ensuring exact diagnosis is obtained. Thus, it is not necessary to repeat photographing. This prevents superfluous amount of X-ray dose from being irradiated to the patient. Furthermore, the ratio of the X-ray transmission dose and film feeding speed is made constant as described above to obtain more uniform film density. Moreover, the system for simultaneously controlling the tube voltage and the tube current serves to achieve automatic exposure and the system for controlling the rotation speed of the rotary arm functions to compensate for the density of the image at the front tooth region as described above. Due to the use of these two control systems, the relationship between the tube voltage and the tube current can be changed, and the rotation speed pattern of the rotary arm can be changed according to the individual differences in dental regions in each patient. As a result, the X-ray photographing apparatus of the present invention has wider applicability of taking good photography and the dynamic range of the X-ray photographing apparatus can be increased.

Having described my invention as related to the embodiment shown in the accompanying drawings, it is my intention that the invention be not limited by any of the details of description, unless otherwise specified, but rather be construed broadly within its spirit and scope as set out in the accompanying claims.

I claim:

1. A dental panoramic X-ray photographing apparatus including a rotary arm having an X-ray generator disposed at one end thereof and having an X-ray film cassette holder disposed at the other end thereof in an opposite relation with each other around an object disposed therebetween, said apparatus being characterized in that it comprises a first control means for controlling the rotation speed of said arm by detecting the rotation position of said arm and a second control means for controlling the tube voltage and the tube current of said X-ray generator by comparing the feeding speed of said X-ray film at said X-ray film cassette holder with the residual X-ray dose which has passed said object and said X-ray film.

2. A dental panoramic X-ray photographing apparatus according to claim 1, wherein said feeding speed of said X-ray film is controlled by a third control means synchronously with said rotation speed of said arm by detecting said rotation position of said arm.

* * * * *